United States Patent [19]

DeLorenzo

[11] Patent Number: 4,928,670
[45] Date of Patent: May 29, 1990

[54] HUMAN KNEE JOINT STABILIZING ORTHOSIS WITH SEMI-RIGID, SUBSTANTIAL ENCASEMENT MEANS FOR LOWER LEG

[76] Inventor: Richard DeLorenzo, 3246 Champions Dr., Wilmington, Del. 19808

[21] Appl. No.: 280,677
[22] Filed: Dec. 6, 1988
[51] Int. Cl.⁵ .............................................. A61F 3/00
[52] U.S. Cl. .................................. 128/80 C; 128/89 R
[58] Field of Search ...................... 128/80 C, 88, 80 F, 128/89 R

[56] References Cited

U.S. PATENT DOCUMENTS

| | | |
|---|---|---|
| 1,446,230 | 2/1923 | Welter . |
| 1,601,659 | 2/1926 | Van Harlingen . |
| 1,622,211 | 3/1927 | Sheehan ............................. 128/80 C |
| 2,460,895 | 2/1949 | Meany . |
| 3,350,719 | 11/1967 | McClure, Jr. . |
| 3,669,105 | 6/1972 | Castiglia . |
| 3,826,251 | 7/1974 | Ross . |
| 3,827,431 | 8/1974 | Pecorella . |
| 3,898,697 | 8/1975 | Whitehead . |
| 3,958,569 | 5/1976 | Vosburgh . |
| 4,144,592 | 3/1979 | Larson .............................. 128/80 C |
| 4,219,892 | 9/1980 | Rigdon . |
| 4,271,831 | 6/1981 | Delbert . |
| 4,323,059 | 4/1982 | Rambert et al. . |
| 4,361,142 | 11/1982 | Lewis et al. . |
| 4,372,298 | 2/1983 | Lerman ............................. 128/80 C |
| 4,387,709 | 6/1983 | Shen .................................. 128/80 C |
| 4,397,308 | 8/1983 | Hepburn . |
| 4,493,316 | 1/1985 | Reed et al. ........................ 128/80 C |
| 4,524,764 | 6/1985 | Miller et al. . |
| 4,553,535 | 11/1985 | Finnieston et al. . |
| 4,554,913 | 11/1985 | Womaek ........................... 128/80 C |
| 4,556,053 | 12/1985 | Irons ................................. 128/80 C |
| 4,565,190 | 1/1986 | Pirmantgen et al. . |
| 4,617,920 | 10/1986 | Carsalade ......................... 128/80 F |
| 4,624,247 | 11/1986 | Ford . |
| 4,686,969 | 8/1987 | Scott . |
| 4,693,239 | 9/1987 | Clover .............................. 128/80 F |
| 4,699,129 | 10/1987 | Aaserude et al. . |
| 4,791,916 | 12/1988 | Paez .................................. 128/80 F |
| 4,793,333 | 12/1988 | Marquette ........................ 128/80 F |

OTHER PUBLICATIONS

Lennox Hill Brace Shop, Inc., "The Lennox Hill Derotation Brace", 4 pages, 1973 (cf. ref. AE, above).
Woodward, H. W., "A New Knee Brace".

Primary Examiner—Edgar S. Burr
Assistant Examiner—Huong Q. Pham

[57] ABSTRACT

A human knee stabilizer having a semi-rigid posteriorly open U-shaped cuff for the upper leg,
a semi-rigid, generally prism-shaped cuff for the lower leg which has a generally triangular cross section,
rigid lateral and medial upper support arms,
  rigid lateral and medial lower support arms,
lateral and medial polycentric pivot structures connecting the upper support arms to the lower support arms,
at least one pre-molded condylar pad,
an interior generally inelastic strap attached at one end to one of the two faces of the lower leg-engaging cuff adjacent a vertically-extending gap in the prism-shaped cuff and having a free end attachable to the other face adjacent the vertically extending gap to complete the encirclement of the wearer's lower leg when the lower leg-engaging cuff is in position on the wearer's lower leg,
an exterior, elastic strap attached at one end to a face of the lower leg-engaging cuff and having a free end attachable to a different face,
an elastic strap attached at one end on one side of the posterior opening of the upper leg-engaging cuff and having a free end attachable to the other side of the posterior opening to complete the encirclement of the wearer's upper leg.

15 Claims, 2 Drawing Sheets

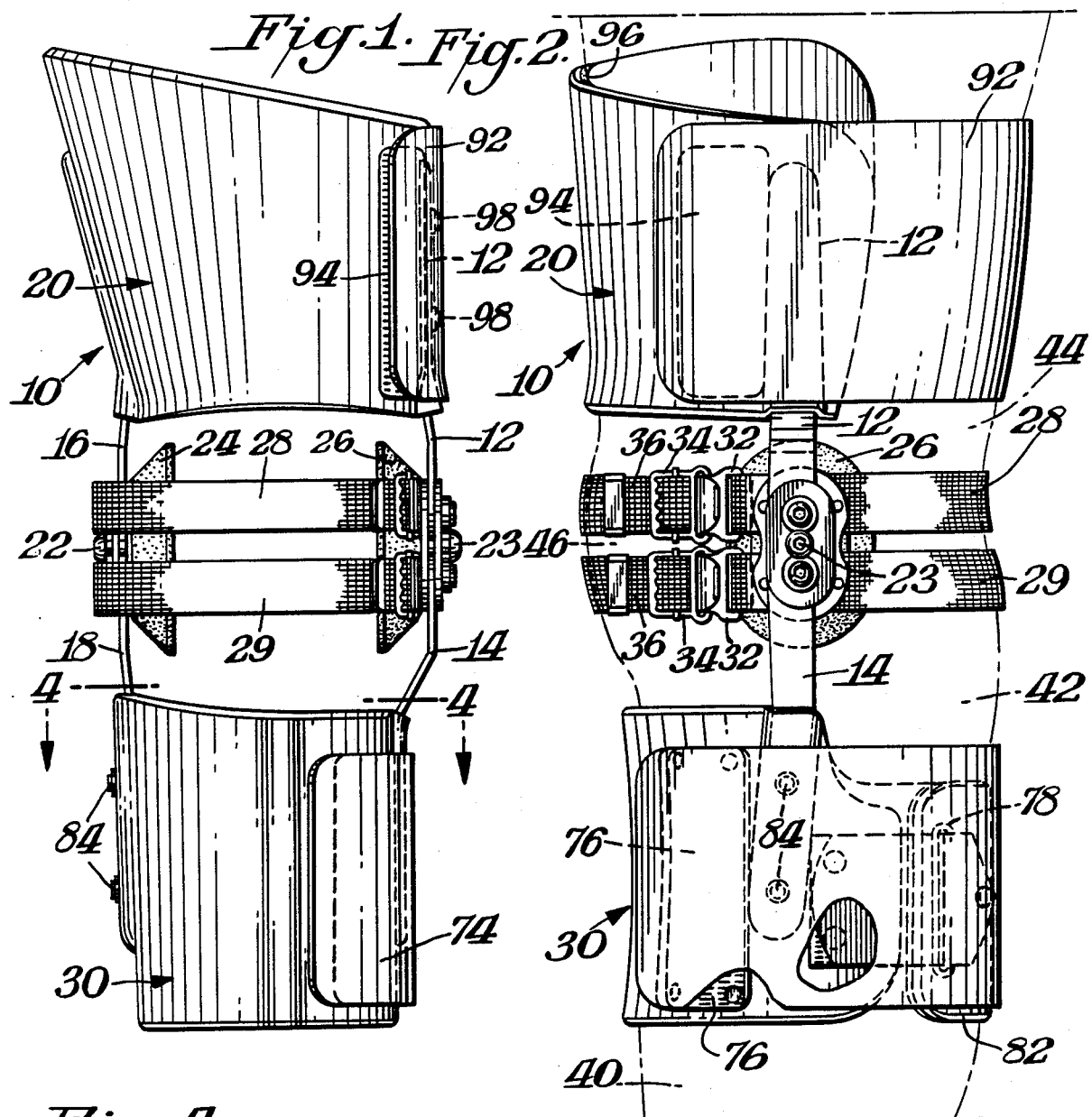
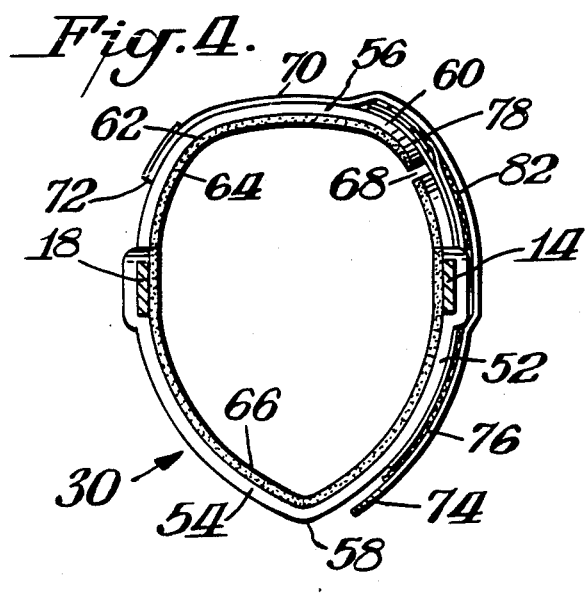

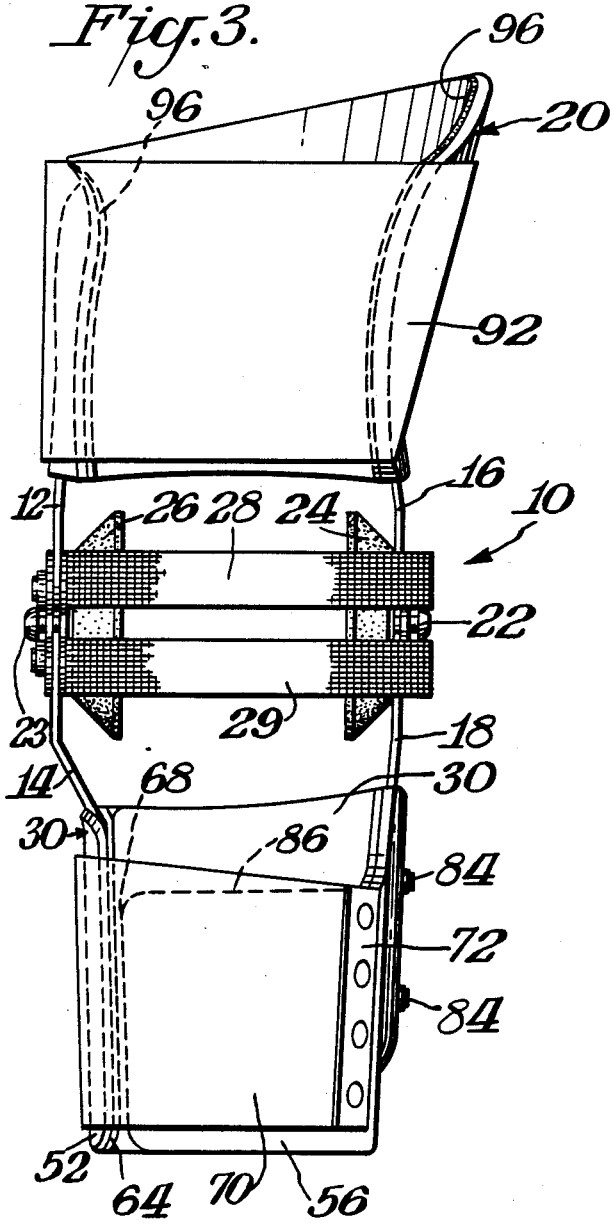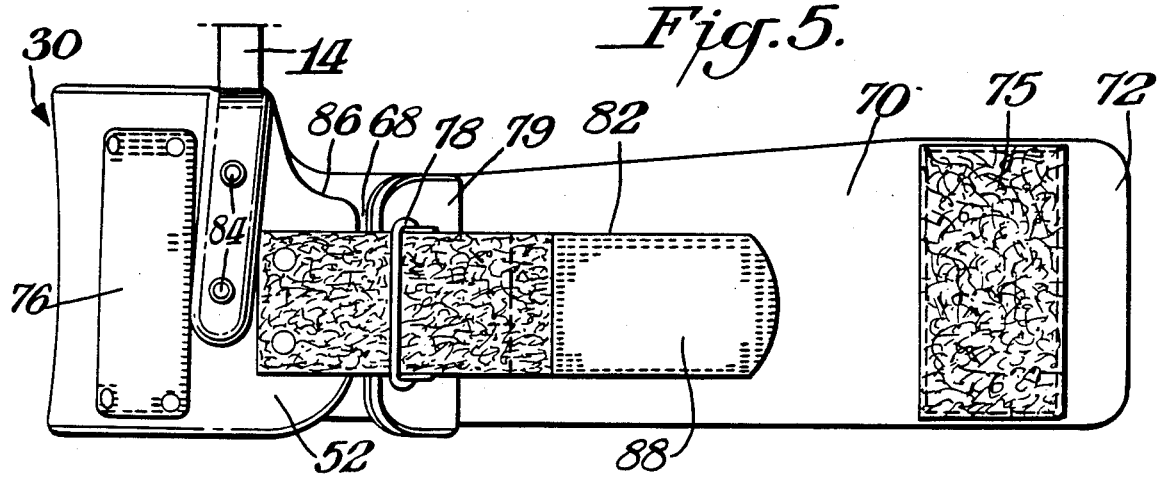

HUMAN KNEE JOINT STABILIZING ORTHOSIS WITH SEMI-RIGID, SUBSTANTIAL ENCASEMENT MEANS FOR LOWER LEG

BACKGROUND OF THE INVENTION

1. Field of the Invention

This invention relates to knee braces or orthoses intended primarily for stabilization of the human knee joint, e.g. a post-operative knee or an injured knee joint having a ligament deficiency or the like. Such orthoses are intended to stabilize the knee joint by protecting it against certain types of harmful motion such as rotational or twisting motion, hyperextension, etc. while nevertheless permitting a degree of normal motion adequate for ordinary activities and even for athletics.

2. Description of the Prior Art

It has long been recognized that patients who have had knee surgery or have suffered knee injuries or damage can benefit significantly from a leg-engaging brace which protects the knee joint from re-injury or further damage by preventing unnatural movements without hindering movements needed for walking, running, etc. Typically, these braces or orthoses are provided with a thigh-engaging component and a calf-engaging component, with side bars or support arms located on both sides of each leg to connect these two components. To permit normal bending of the knee or swinging back and forth of the lower leg, the support arms or side bars have pivot devices which act much like hinges but in addition define a useful range of motion about a horizontal axis through the knee. Further support for the knee is provided by elastic straps which encircle or partially encircle the leg and are attached at various locations on the brace. Convenient fastening and unfastening of these straps is typically provided with modern synthetic fabric devices such as VELCRO fasteners, which are made up of an engagement means comprising a great multitude of tiny plastic loops or hooks and/or a raised nap, so that mated fabric surfaces will engage each other.

In recent years, the development of these braces has been progressing very rapidly, with the result that the patent literature in this field has become extremely voluminous. It has become difficult to cover, in any discussion of reasonable length, even a representative sampling of relevant patent disclosures.

Despite the growth of knowledge and skill in this art, problems for the wearers of knee orthoses and for their physicians and therapists remain to be solved. It is particularly difficult to design a knee brace which will prevent hyperextension, undue twisting of the knee joint, etc. and yet will be simple, light in weight, non-slipping, easy to manufacture, comfortable to wear, and capable of permitting great ease of normal motion in a any desired direction, e.g. in strenuous athletic contests. Knee braces which provide all the desired protection with reasonable comfort and good freedom of normal motion tend to be heavy or complex in structure. The simpler braces, on the other hand, may fail to provide adequate protection against certain unnatural movements such as hyperextension. Alternatively, the simpler devices may be subject to slippage, twisting or rotation movement about the vertical axis of the leg. Moreover, all modern knee braces intended for athletic use must accommodate major dynamic changes such as the changes in muscle shape and volume which occur through a very wide range of motion.

Because of the extensive development of this art particularly during the last five to ten years, any list of patent references is necessarily incomplete, even if intended as only a sampling of the available patent literature, but the following list can serve as an introduction to the modern, relatively sophisticated types of knee orthoses.

| | | |
|---|---|---|
| 3,669,105 | (Castiglia) | June 13, 1972 |
| 4,361,142 | (Lewis et al) | Nov. 30, 1982 |
| 4,372,298 | (Lerman) | Feb. 8, 1983 |
| 4,493,316 | (Reed et al) | Jan. 15, 1985 |
| 4,554,913 | (Womack et al) | Nov. 26, 1985 |
| 4,556,053 | (Irons) | Dec. 3, 1985 |
| 4,565,190 | (Pirmantgen et al) | Jan.21, 1986 |
| 4,624,247 | (Ford) | Nov. 25, 1986 |
| 4,686,969 | (Scott) | Aug. 18, 1987 |

SUMMARY OF THE INVENTION

Briefly, the preferred embodiments of human knee braces or orthoses or stabilizers of this invention comprise:

a semi-rigid, posteriorly open U-shaped cuff for the upper leg, a semi-rigid, generally prism-shaped cuff for the lower leg which has a generally triangular cross-section (e.g. a cross-section with the shape of a rounded triangle having rounded corners and arcuate sides) for substantially encircling and substantially encasing the shin and calf of the wearer (this semi-rigid cuff has a vertically-extending slit or gap and has sufficient flexibility to be bent open for donning by the wearer);

rigid lateral and medial support arms connecting the two cuffs and provide an articulation in the form of a conventional polycentric pivot means;

a molded condylar pad or pads located medially and/or laterally and attached to one or both of the inside face or faces of the polycentric pivot means to maintain constant contact and control of the knee throughout the range of motion of the wearer's knee joint; and a system of straps designed to provide complete encirclement of the upper leg (femur) and the lower leg (tibia) while providing firm support, contact and suspension of the entire orthosis throughout the range of motion. The system of straps includes an inelastic, inextensible strap for the lower leg (tibial) cuff as well as elastic straps which accommodate changes in muscle shape and volume throughout the range of motion of the wearer's knee and leg. The triangular shape of the calf-shin-encompassing component (which includes the semi-rigid cuff and the inelastic strap) is an important aspect of this invention, because it helps to secure the orthosis in place on the wearer's leg, prevent slippage, and most importantly provides a non cylindrical attachment base to control undesired rotation about the axis of the knee in the coronal plane.

A particularly preferred embodiment of a knee stabilizer of this invention comprises a padded, semi-rigid full-encompassing triangular prism-shaped skin-calf component connected medially and laterally by the polycentric pivot devices. As noted above, a molded condylar pad or pads are attached (preferably as rigidly as possible) to the inner surface or surfaces of the polycentric pivots to maintain constant contact and control of the knee throughout the range in motion and to inhibit slippage. The semi-rigid thigh (femur) component surrounds roughly two-thirds (roughly 240°) of the upper leg (thigh), the posterior third being open. Encirclement of the thigh is completed with an elastic strap provided with a VELCRO fastener, so that complete encirclement (providing support and suspension) will nevertheless not interfere with any dynamic changes which might take place in the muscles in the thigh. The calf-shin component, on the other hand, provides much fuller encirclement (indeed, encasement) of the lower leg. The amount of encirclement (encasement) is preferably at least seven-eights or at least about 315° and can be 350° or more; for example, the vertically-extending slit or gap in the lower leg cuff need not provide a visible opening in the cuff, because of the semi-rigid (i.e. at least partially flexible) nature of the cuff, which permits the wearer to bend the sides of the cuff open and slip it onto his leg. This slit or gap can be located laterally or medially (preferably laterally). When the calf-shin component is in place, encirclement is completed with the inelastic strap, and in addition, an elastic strap is preferably provided for superposition over the inelastic strap to impart additional support and suspension while dynamically accommodating changes in muscle shape and volume throughout the range of motion of the wearer's leg and knee. The triangular shape of the calf-shin component with intimately molded areas across the medial flare of the tibia, the lateral aspect of the tibia, and peroneus longeus musculature, and the flattening and compression of the gastroc musculature posteriorly (just inferior to the poplitial area) locks the cuff, and to a considerable extent the entire brace, securely on the shin. This in combination with at least one intimately fitting condylar pad, and in cooperation with the polycentric pivots and molded thigh component provides total control of knee motion in varum, valgum, rotation (pivot shift) and extension. Medial-lateral control is provided by the condylar pad or pads with opposing forces at the superior and inferior aspects of the medial and lateral portion of the thigh and shin-calf components.

It is particularly preferred that a pair of knee-encircling elastic straps pass from the ipsilateral joint upright around the contralateral joint, one inferior and one superior to the patella, and one secured to the condyle pad component with adjustable buckles, providing constant support, contact, and suspension of the brace throughout the range of motion of the wearer.

BRIEF DESCRIPTION OF THE DRAWING

In the accompanying Drawing, wherein, for convenience, a stabilizer for the left knee is illustrated:

FIG. 1 is an anterior (front) elevational view illustrating a knee stabilizer of this invention;

FIG. 2 is the lateral (for left leg) side elevational view of FIG. 1;

FIG. 3 is a posterior (rear) elevational view of the left knee stabilizer of FIGS. 1 and 2;

FIG. 4 is a cross-sectional view taken along line 4—4 of FIG. 1 showing a top plan view of the lower cuff of a left knee stabilizer of this invention; and FIG. 5 is a lateral (side) elevational view of the lower cuff shown in FIG. 4, showing straps in an unfastened position.

DETAILED DESCRIPTION

As indicated previously, the design of the lower cuff (which surrounds the calf and shin) is a very important aspect of this invention. This lower cuff provides at least two secure pressure points to guard against, among other things, pivot shift and hyperextension of the knee. An anterior pressure point is provided by a flat spot in the interior of the cuff which matches very closely the flat frontal aspect of the tibia. The posterior pressure point is provided by a calf-encasing portion of the cuff which firmly engages the calf just below the knee. It is particularly preferred that the upper edge of this posterior portion of the lower cuff be distally further removed from the knee joint than the upper edge of the anterior portion of the lower cuff; indeed, the anterior edge or edges is or are just below the patella or even touching the distal, anterior aspect of the patella.) The slit in this lower cuff (which permits easy donning of the cuff by the wearer) is located laterally. A plan view of the lower cuff shows a rounded triangle (not a circular annulus), so that it will grip the tibia securely, and the slit (preferably a narrow slit) which permits opening of the cuff to insert the calf is preferably more than 90° from the anteriorly-located vertex of this triangle, but is considerably less than 180° from this vertex.

These features of the lower cuff, in combination with the other features described previously, provide a lightweight, simple, extremely effective brace or orthosis which is resitant to slippage and is suitable for use in both normal and vigorous activities, including athletics.

Throughout this disclosure, the term "upper leg" refers to the thigh or, in skeletal terms, the femur, i.e. from the hip joint distally as far as the knee joint, and the term "lower leg" refers to the calf and shin, which in skeletal terms includes at least two bones, the larger of which is the tibia and extends from the knee joint distally as far as the ankle joint.

The terms "lateral" and "medial" are used in the conventional anatomical manner, as are "distal" and "proximal".

Turning now to the Drawing, wherein like numerals denote identical parts in the various views, it will be noted from FIGS. 1, 2, and 3 that a knee orthoris or stabilizer 10 of this invention comprises a U-shaped, upper leg-engaging cuff 20 and a lower leg-engaging cuff 30, rigid lateral and medial upper support arms 12 and 16 integral with the upper leg-engaging cuff 20, rigid lateral and medial lower support arms 14 and 18 integral with the lower leg-engaging cuff 30, medial and lateral polycentric pivot means 22 and 23, and bilateral pre-molded condylar pads 24 and 26. Moreover, knee stabilizer 10 is provided with a system of straps (described subsequently) to provide firm encirclement of the leg of the wearer.

The upper leg-engaging cuff 20 is open posteriorly, the wide gap between the lateral and medial sides being roughly the posterior third of cuff 20. Encirclement of the wearer's thigh is completed with elastic strap 92 which is attachable near its free end by virtue of the mating surface of a VELCRO fastener mounted on the lateral side or face of the cuff 20. Attachment of upper support arms 12 and 16 to cuff 20 is provided by rivets 98 (FIG. 1). Cuff 20 is semi-rigid because it is fabricated from a heavy-gauge polymeric sheet material which has a degree of flexibility but provides firm support and resistance to excessive bending or deformation by virtue of its considerable thickness. The inner surface of cuff 20 is, on the other hand, covered with a deformable liner 96 (most easily seen in FIG. 3) which conforms comfortably to the wearer's thigh. Support arms 12 and 16 (and also lower support arms 14 and 18) can be fashioned from a rigid material such as metal strips.

The polycentric pivot means 23 and 22 can be of a conventional design such as one of the designs shown in U.S. Pat. Nos. 3,826,251 (Ross), issued July 30, 1974, 4,493,316 (Reed), issued Jan. 15, 1985, 4,554,913 (Womack et al), issued Nov. 26, 1985, 4,556,053 (Irons), issued Dec. 3, 1985, or 4,699,129 (Aaserude et al), issued Oct. 13, 1987. In the particular embodiment illustrated in the Drawing, pre-molded condylar pads 24 and 26 are firmly attached to the inside of each polycentric pivot device (i.e. polycentric pivot means 23 and 22), although it is not essential that a condylar pad be attached bilaterally. For some wearers, a single condylar pad (located either medially or laterally) will suffice to prevent or hinder rotational and/or vertical flippage of knee stabilizer 10. It is preferred that condylar pads 24 and 26 be fabricated from an elastomeric material such as a synthetic rubber. For extra conformity to the femoral condyles of the wearer, at least the innermost portions of condylar pads 24 and 26 can comprise a foamed or cellular elastomer. (Similarly, the conformable liner 96 of cuff 20 can be a foamed or cellular elastomeric material; the elastic strap 92, on the other hand, is preferably cut from a solid rubber sheet made from a rubber latex.)

In the preferred embodiment shown in the drawing, elastic straps 28 and 29 (preferably made of a stretchy fabric) are attached to one of the polycentric pivots; in the case of the embodiment shown, straps 28 and 29 are attached to the lateral polycentric pivot means 23. The tabbed, free ends 36 of straps 28 and 29 are designed to circle the knee joint and be attached to the anterior side of pivot means 20 by means of adjustable buckles 32 which include adjustable hook elements 34 provided with teeth for engagement of straps 28 and 29. In the configuration shown in FIGS. 1-3 of the Drawing, the superior strap passes over the proximal aspect of the patella 46 (shown in phantom in FIG. 2) of the wearer's leg 40 (also shown in phantom in FIG. 2), i.e. the portion of the patella 46 immediately adjacent the upper leg 44 (FIG. 2, in phantom). Strap 29 passes over the distal aspect of patella 46 (FIG. 2), i.e. the aspect immediately adjacent the lower leg 42 (FIG. 2). However, other arrangements of knee-encircling straps are within the scope of this invention, including criss-crossed straps, in which case strap 28 would pass distally below patella 46, while strap 29 would pass proximally, superior to patella 46.

Many of the particularly novel aspects of this invention can be understood by consulting FIGS. 4 and 5 and the lower (distal) half of FIGS. 1-3. The attachment of lower leg-engaging cuff 30 to the rest of knee stabilizer 10 by means of lower support arms 14 and 18 and rivets 84 (FIGS. 1-3) is more or less conventional, but cuff 30 is provided with various unique features to lock knee stabilizer 10 securely on the wearer's leg and to provide, in combination with the other elements of stabilizer 10, excellent control over undesirable types of knee motion. As noted previously, medial-lateral control is provided by the condylar pad or pads with opposing forces at the superior and inferior aspects of the medial and lateral portion of cuffs 20 and 30; rotation and pivot shift control is maintained in part by the unusual shape of the lower leg-engaging cuff 30 in combination with the condylar pad or pads and the medial-lateral aspects of upper leg-engaging cuff 20 and the strap 92; and knee extension control is provided by posteriorly directed forces from the anterior thigh, the anterior aspect of the lower leg-engaging cuff 30, and an anteriorly directed force at the superior aspect of the posterior portion of cuff 30.

To achieve these objectives, cuff 30 is shaped much like a triangular prism extending upwardly from a lower triangular face. Viewed from above, (see FIG. 4), it can be seen that cuff 30 has a cross-section which resembles a triangle having rounded corners and arcuate sides. The vertex 58 of this triangle is the least rounded of the three corners, because it is designed to be located at the sharp anterior border of the shaft of the wearer's tibia. Lateral and medial sides of this cross-section (FIG. 4) correspond to lateral and medial faces of the prism-like shape of cuff 30, while the base of the triangular cross-section corresponds to posterior face 56 of cuff 30. As in the case of the upper leg-engaging cuff 20, cuff 30 is made of a semi-rigid polymeric material lined with a conformable liner 64 which is preferably shaped to fit the wearer's lower leg 42 (FIG. 2) as comfortably and accurately as possible, e.g. by a custom-forming procedure. Extending medially from vertex 58 is a vertically-extending, substantially planar portion 66 of conformable liner 64. This planar portion 66 is thus intimately conformed to the medial flare of the wearer's tibia, and the prism-shape of cuff 30 virtually encases the anterior aspect of the tibia and peroneus longus musculature, thus providing an anterior pressure point (without causing undue discomfort to the wearer), the rear pressure point being provided by the semi-rigid posterior face 56.

An exterior elastic strap 70 has a firmly attached or anchored end 72 in close proximity to the medial/posterior corner 62 and is part of a strapping system which will be discussed subsequently. Near the posterior/lateral corner 60 is a vertically-extending gap 68 which is extremely narrow and can amount to less than 10° (preferably less than 5°) of the entire lower leg encirclement. Indeed, it is permissible for the two sides of the gap to be in contact with each other, so long as the wearer has no difficulty prying open cuff 30 for placement on the lower leg.

The strapping system for cuff 30 can best be understood by referring to FIG. 2 (which has parts broken away to illustrate more effectively some of the aspects of this strapping system) and FIG. 5, which shows the straps in the open (unfastened) position. As noted previously, strap 70, which is elastic, is an exterior strap superimposable upon an inner, substantially inelastic and inextensible strap 82. Strap 82 is anchored or firmly attached at one end and has a free end provided with a mating surface 88 for a VELCRO fastener (FIG. 5). Although strap 82 is shown in FIG. 5 in an unfastened position, this strap 82 has been passed through an elongated, rigid loop or buckle means 78, this rigid elongated loop 78 being integral with cuff 30 by virtue of its firm attachment to a short, inelastic stub-like strap 79. Strap 82 is provided with a mating surface for the fabric fastening (VELCRO) means 88, so that when strap 82 is doubled back upon itself, the free end can be fastened securely near the anchored end. After strap 82 has been fastened in this manner, strap 70 can be placed over it, so that the raised nap attachable mating surface 75 will mate with the other mating element 76 attached to cuff 30. Strap 70 will then cover strap 82 completely, as is clearly shown by FIG. 2.

It will be noted that the posterior face 56 of cuff 30 is somewhat smaller than the other two faces. The upper edge of the lateral and medial faces 52 and 54 is in close proximity to the distal aspect of patella 46, but upper edge 86 of the posterior face is more distally located (when in place) and is thus below the knee joint. It is not necessary (and ordinarily not desirable) for the pressure provided by the posterior face to extend all the way up to the posterior aspect of the knee joint. To do so would inhibit Fletion of the knee unnecessarily.

Although the strapping system shown in detail in FIG. 5 is illustrated only for the lower leg-engaging cuff 30, a similar inelastic or relatively inelastic strap means (not shown) can be provided in the case of the upper leg-engaging cuff 20. In this case, as in the strapping system shown in FIG. 5, the inelastic or relatively inelastic strap would preferably be the interior strap, and the elastic strap 92 would be superimposed upon it when both straps were fully fastened.

Particularly preferred knee stabilizers of this invention are believed to provide extremely effective knee encirclement by virtue of the elastic straps 28 and 29, which can pass from the ipsilateral joint upright around the contralateral joint, one inferior to and one superior to the patella, and one secured to the condyle pad with the adjustable buckle, thereby insuring further the constant support, contact and suspension of knee stabilizer 10 throughout the range of motion. However, in some applications of the knee stabilizers of this invention, these knee-encircling straps can be omitted.

A knee orthosis of this invention also provides excellent stability by virtue of its extensive contact with the upper and lower leg. As will be apparent from the Drawing, the upper leg-engaging cuff is normally somewhat longer than the lower leg-engaging cuff, but both cuffs 20 and 30, in combination with their strapping systems, provide considerable leg contact. Both cuffs 20 and 30 are of one-piece construction for strength and firmness of support.. Cuff 20 engages at least the distal quarter of the wearer's thigh, and cuff 30 engages at least the proximal quarter of the wearer's tibia. Many other desirable and advantageous features of this invention will become apparent from the foregoing disclosure. Moreover, while the foregoing disclosure explains important aspects of this invention in considerable detail for purposes of illustration, it will be understood by those skilled in the art that many of these details may be varied without departing from the spirit and scope of the invention.

What is claimed is:

1. A human knee stabilizer comprising:
   a semi-rigid, posteriorly open U-shaped, upper leg-engaging cuff having medial and lateral sides;
   a semi-rigid, generally triangular prism-shaped lower leg-engaging cuff constructed and arranged such that: the vertex of the triangular cross-section of the triangular prism-shaped lower leg-engaging cuff is generally located at the sharp anterior border of the shaft of the wearer's tibia and the lateral and medial faces corresponding to the lateral and medial sides of said triangular cross-section engage the lateral and medial sides of the wearer's lower leg, while the posterior face corresponding to the base of said triangular cross-section engages the posterior of the wearer's calf muscle, and said cuff encircles at least 315° of the wearer's calf and shin and thereby defines a vertically-extending gap in said cuff remote from said vertex and in closely-spaced relation to the corner at the intersection of said base and a said of said triangular cross-section, to facilate engagement of the wearer's lower leg with said cuff, the interior medial face of the lower leg-engaging cuff including a vertically-extending, substantially planar portion, medially extending from said vertex, for conforming to the anterior, planar-shaped medial flare of the wearer's tibia;
   rigid lateral and medial upper support arms integral with the lateral and media sides of the upper leg-engaging cuff and extending downwardly from said sides;
   rigid lateral and medial lower support arms integral with the lateral and medial faces of said lower leg-engaging cuff and extending upwardly from said faces;
   lateral and medial polycentric pivot means connecting the upper support arms to the lower support arms to complete the lateral and medial support and to provide range-of-motion control, each said polycentric pivot means including an inner face arranged to face the wearer's lateral or medial femoral condyle;
   at least one pre-molded condylar pad attached to a said inner face for engaging a said condyle;
   an interior generally inelastic strap attached at one end to one of the two faces of the lower leg-engaging cuff which is adjacent said vertically-extending gap and having a free end attachable to the other face adjacent said vertically extending gap to complete the encirclement of the wearer's lower leg when the lower leg-engaging cuff is in position on the wearer's lower leg;
   an exterior, elastic strap attached at one end to a face of the lower leg-engaging cuff and having a free end attachable to a different face, for superposition upon said interior generally inelastic strap when the free end of said inelastic strap is attached; and
   an elastic strap attached at one end on one side of the posterior opening of the upper leg-engaging cuff and having a free end attachable to the other side of the posterior opening to complete the encirclement of the wearer's upper leg.

2. Knee stabilizer according to claim 1, said knee stabilizer further comprising a pair of elastic knee-encircling straps both attached at one end to the inner face of a said polycentric pivot means, both said knee-encircling straps having free ends which are attachable to attachment means integral with the same polycentric pivot means to which the opposite ends are attached.

3. Knee stabilizer according to claim 2, wherein the pair of knee-encircling straps comprises a strap adapted to be positioned proximally to the wearer's patella and a strap arranged to be positioned distally to wearer's patella.

4. Knee stabilizer according to claim 1, wherein the lower leg-engaging cuff encircles and encases at least about 350° of the lower leg and wherein said triangular cross-section of said cuff has rounded corners and arcuate faces constructed and arranged to conform to the shape of the calf and shin.

5. Knee stabilizer according to claim 4, wherein the inner faces of the upper leg-engaging cuff and the lower leg-engaging cuff are padded with a material comformable to the shape of the wearer's leg.

6. Knee stabilizer according to claim 1, wherein a said pre-molded condylar pad is attached to the inner face of both the medial and lateral polycentric pivot means.

7. Knee stabilizer according to claim 1, wherein said upper leg-engaging cuff engages at least the distal quarter of the wearer's upper leg, and said lower leg-engaging cuff engages at least the proximal quarter of the wearer's lower leg.

8. Knee stabilizer according to claim 1, wherein said vertically-extending gap in the lower leg-engaging cuff is located at least 90° but less than 180° from said vertex.

9. Knee stabilizer according to claim 8, wherein said gap is located in the lateral face of the lower leg-engaging cuff.

10. Knee stabilizer according to claim 1, wherein the proximal or upper edges of said lateral and medial faces of said lower leg-engaging cuff are adjacent to the patella of the wearer, but the proximal or upper edge of the posterior face of said lower leg-engaging cuff is more distal and is below the knee joint, when the knee stabilizer is in position on the wearer's leg.

11. Knee stabilizer according to claim 1, wherein the posterior face of the lower leg-engaging cuff is provided with an elongated rigid loop as a strap tensioning means; wherein said interior, generally inelastic strap is attached at one end to the lateral face of the lower leg-engaging cuff;
and wherein the secure encirclement is obtained by inserting said inelastic strap through the rigid loop, doubling it back and fastening it to said lateral face.

12. In a human knee stabilizer comprising an upper component comprising a semi-rigid U-shaped, upper leg-engaging cuff and an elastic strap attached thereto to complete the encirclement of the upper leg; a lower component attached to said upper component with rigid lateral and medial support arms integral with said upper and lower components and provided with lateral and medial polycentric pivot means for articulation, said lower component comprising:

a semi-rigid, generally triangular prism-shaped lower leg-engaging cuff of one-piece construction with a vertically-extending gap, said lower leg-engaging cuff being constructed and arranged such that: the triangular cross-section of the triangular prism-shaped lower leg-engaging cuff has rounded corners and arcuate sides, the vertex of said triangular cross-section being generally located at the sharp anterior border of the shaft of the wearer's tibia and the lateral and medial faces corresponding to the lateral and medial sides of said triangular cross-section engage the lateral and medial sides of the wearer's lower leg, while the posterior face corresponding to the base of said triangular cross-section engages the posterior of the wearer's calf muscle, and said cuff encircles at least 350° of the wearer's calf and shin and thereby defines said vertically-extending gap in said cuff located at least 90° but less than 180° from said vertex and in closely-spaced relation to the corner at the intersection of said base and a said side of said triangular cross-section, to facilitate engagement of the wearer's lower leg by said cuff, the interior medial face of the lower leg-engaging cuff including a vertically extending, substantially planar portion, medially extending from said vertex, for conforming to the anterior, planar-shaped medial flare of the wearer's tibia, the inner faces of the lower leg-engaging cuff being padded with a material conformable to the shape of the wearer's leg, and the interior medial face of the lower leg-engaging cuff being constructed and arranged to provide a vertically-extending, substantial planar portion, medially extending from said vertex, for conforming to the anterior, planar-shaped medial flare of the wearer's tibia;

said lower leg-engaging cuff being long enough in its axial dimension to engage at least the proximal quarter of the wearer's lower leg;

the proximal or upper edges of said lateral and medial faces of said lower leg-engaging cuff being adjacent to the patella of the wearer, but the proximal or upper edge of the posterior face of said lower leg-engaging cuff being more distal and hence below the knee joint, when the knee stabilizer is in position on the wearer's leg;

an interior generally inelastic strap attached at one end to one of the two faces of the lower leg-engaging cuff which is adjacent said vertically-extending gap and having a free end attachable to the other face adjacent said vertically extending gap to complete the encirclement of the wearer's lower leg when the lower leg-engaging cuff is in position on the wearer's lower leg; and an exterior, elastic strap attached at one end to a face of the lower leg-engaging cuff and having a free end attachable to a different face, for superposition upon said interior generally inelastic strap when the free end of said inelastic strap is attached.

13. Knee stabilizer according to claim 12, said knee stabilizer further comprising a pair of elastic, knee-encircling straps both attached at one end to the inner face of a said polycentric pivot means, both the knee-encircling straps having free ends which are attachable to attachment means integral with the same polycentric pivot means to which the opposite ends are attached.

14. Knee stabilizer according to claim 12, wherein a pre-molded condylar pad is attached to the inner face of a said polycentric pivot means.

15. Knee stabilizer according to claim 12, wherein said gap is located in the lateral face of the lower leg-engaging cuff.

* * * * *